United States Patent [19]

Wehrmeister

[11] 4,166,121
[45] Aug. 28, 1979

[54] METHOD OF CONTROLLING THE GROWTH OF BACTERIA AND FUNGI

[75] Inventor: Herbert L. Wehrmeister, Terre Haute, Ind.

[73] Assignee: International Minerals & Chemical Corporation, Terre Haute, Ind.

[21] Appl. No.: 942,206

[22] Filed: Sep. 14, 1978

Related U.S. Application Data

[60] Division of Ser. No. 880,687, Feb. 23, 1978, Pat. No. 4,148,803, which is a continuation-in-part of Ser. No. 728,695, Oct. 1, 1976, abandoned.

[51] Int. Cl.² .......................... A01N 9/00; A01N 9/02; A01N 9/20; A01N 9/24
[52] U.S. Cl. ..................................... 424/269; 424/329; 424/330
[58] Field of Search .................... 424/269, 320, 329

[56] References Cited

U.S. PATENT DOCUMENTS

| 2,954,314 | 9/1960 | Metzger | 424/325 |
| 3,256,147 | 6/1966 | Meiser et al. | 260/577 |
| 4,013,580 | 3/1977 | Hayashi et al. | 260/577 |

FOREIGN PATENT DOCUMENTS

| 2008130 | 9/1971 | Fed. Rep. of Germany | 424/325 |
| 2054661 | 3/1972 | Fed. Rep. of Germany | 424/325 |

Primary Examiner—Allen J. Robinson
Attorney, Agent, or Firm—Robert H. Dewey; Howard E. Post

[57] ABSTRACT

The product prepared by the process consisting of the steps of (a) reacting a nitroalcohol of the formula

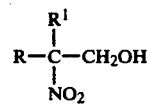

where R and $R^1$ can be hydrogen, methyl, ethyl or hydroxymethyl in about a 1:1 mole ratio with an alkylamine represented by the formula $R^2NH_2$ where $R^2$ is alkyl of from 1 to 4 or more carbon atoms or phenyl, benzyl, toluyl, or xylyl at about 50°–70° thereby effecting formation of a nitroalkylamine; (b) reacting the nitroalkylamine with nitrous acid at about 0°–5°, thereby forming a nitroso compound; and (c) reducing the nitroso compound.

17 Claims, No Drawings

METHOD OF CONTROLLING THE GROWTH OF BACTERIA AND FUNGI

CROSS-REFERENCE TO RELATED APPLICATIONS

This is a division of copending application Ser. No. 880,687, filed Feb. 23, 1978, now U.S. Pat. No. 4,148,803 issued Apr. 10, 1979, which is a continuation-in-part application of Ser. No. 728,695, filed Oct. 1, 1976, now abandoned.

BACKGROUND OF THE INVENTION

This invention relates to a method of controlling the growth of bacteria. In a particular aspect, this invention relates to a method of controlling the growth of bacteria using a product prepared by a disclosed process.

Numerous compounds have been disclosed for controlling the growth of bacteria. However, it has long been the experience of workers in this field that the bacteria, after prolonged exposure to toxic compounds at sub-lethal levels, often develop a resistance to them. Consequently, there is a continuing need for new products useful for controlling the growth of bacteria.

SUMMARY OF THE INVENTION

It is an object of this invention to provide a method of controlling the growth of bacteria.

It is another object of this invention to provide a method of controlling the growth of microorganisms using a product prepared by a disclosed process.

Other objects will be apparent to those skilled in the art from the disclosure herein.

It is the discovery of this invention to provide a method of controlling the growth of bacteria using a product prepared by the process of reacting a nitroalcohol of the formula

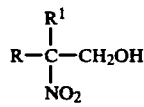

where R and $R^1$ can be hydrogen, methyl, ethyl or hydroxymethyl with an amine represented by the formula $R^2NH_2$ where $R^2$ is alkyl of from 1 to 4 or more carbon atoms or phenyl, benzyl, toluyl, or xylyl thereby effecting formation of a nitroalkylamine, (b) reacting the nitroalkylamine with nitrous acid at about 0°–5°, thereby forming a nitroso compound; and (c) reducing the nitroso compound.

DETAILED DISCUSSION

The compounds of the present invention are prepared using a nitroalcohol and an alkylamine of from 1 to 4 carbon atoms or an aromatic amine, e.g. aniline, toluidine, xylidine or benzylamine as the starting materials. In general, a nitroalcohol represented by the formula

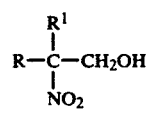

where R and $R^1$ have the same meaning as set forth above, is reacted in about a 1:1 mole ratio with an alkylamine represented by the formula $R^2NH_2$. The reaction between the nitroalcohol and the amine, is carried out in aqueous solution at elevated temperatures, e.g. of from about 50°–70° for a time sufficient to effect formation of a nitroamine (Compound I, below). The product is recovered by any suitable means, e.g. by evaporation or by extraction with benzene. It can be further purified if desired, e.g. by recrystallization from benzene, or it can be used as is for the next step.

The nitroamine obtained by the foregoing reaction is converted to the nitroso compound by reacting it with nitrous acid at about 0°–5°, as is known in the art. After formation of the nitroso compound, it is recovered by filtration. If preferred it can be purified by recrystallization. Generally, however, it is unnecessary to purify the nitroso compound.

The nitroso compound formed as described above is dissolved in a suitable solvent, e.g. a lower alcohol, and reduced by any convenient means, many of which are known. A preferred method of reduction is by catalytic hydrogenation at elevated temperature, e.g. 40°–60° in the presence of hydrogen and finely divided palladium, and at elevated pressure, e.g. 500–2000 psig, until hydrogen absorption virtually ceases. Surprisingly, the nitro group is reduced only partially and the compound thereby obtained is then recovered by evaporation and purified to the extent desired.

The preparation of the nitroso compound is represented by the following equations:

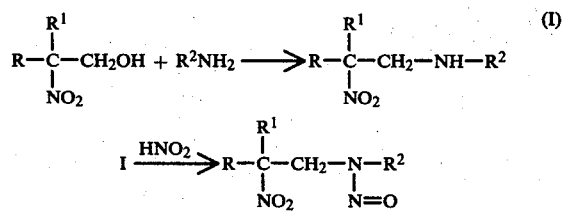

The structure of the compound formed by hydrogenation of the nitrosoamine has not been established. It is believed that the triazolidine represented by the formula

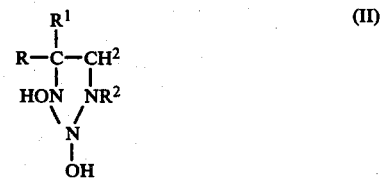

may be one of the products and it is further believed that II may be in equilibrium with the open chain compound

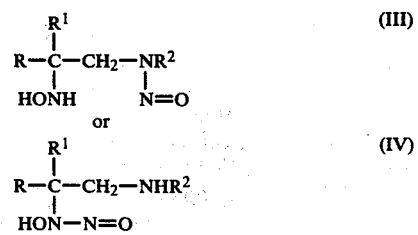

It is also contemplated that compounds II, III and IV may all be in equilibrium. Such compounds where $R^2$ is of 4 or more carbon atoms are also effective against fungi. The compound preferred for the practice of this invention is the one wherein R, $R^1$ and $R^2$ are methyl.

The nitroalcohols used in preparing the compounds of this invention include 2-nitro-1-ethanol; 2-nitro-2-methyl-1-propanol; 2-nitro-1-butanol; 2-nitro-2-methyl-1,3-propanediol; 2-nitro-2-ethyl-1,3-propanediol and tris(hydroxymethyl)nitromethane. These compounds are known in the art and most of them are commercially available. The usual commercial grades are suitable for the practice of this invention.

The alkylamines used in the practice of this invention are primary amines and include methylamine, ethylamine, the propylamines and the butylamines. They are commercially available and the usual commercial grades are suitable for the practice of this invention. Methylamine is a gas at ambient temperatures and pressures and is available either as an anhydrous compressed gas or as an aqueous solution. The solution is generally preferred as being more convenient to handle.

The compounds useful in the practice of this invention are generally effective to combat the growth of bacteria at low concentrations, e.g. 10 ppm. There is, of course, no upper limit to the amount that can be used but generally they become uneconomical above about 5000 ppm and, accordingly, a use concentration of 10–5000 ppm is contemplated. Generally, however, a concentration between 100 and 2000 ppm is preferred and a concentration of 500–1000 ppm is particularly preferred.

The compounds produced by the process of this invention are conveniently applied to the environment inhabited by microorganisms as an aqueous solution or dispersion. They are particularly effective in aqueous systems such as starch adhesives and solutions, drilling muds for the petroleum industry and in water-dilutable cutting oils based on petroleum hydrocarbons.

These compounds are also soluble in, e.g. alcohols, ketones and most other organic solvents, including hydrocarbons. Solutions of the water-insoluble compounds in such solvents can be used in substantially non-aqueous or 2-phase systems when desired.

The anti-microbial compounds of this invention can be used without dilution for the control of a wide variety of organisms. Preferably, however, they are used in a dispersed form in a suitable extending agent.

The method of combatting microorganisms of this invention comprises application of the compound to a substratum infested with the microorganisms to be combatted or to a substratum to be protected from infestation with the microorganisms. The term substratum as used herein is intended to mean the environment or medium upon which an organism grows. No attempt has been made to determine if the products actually cause the death of the organism or merely prevent their growth.

The term "dispersed" is used herein in the widest possible sense. When the anti-microbial agents of this invention are said to be dispersed, it can mean that the particles of the anti-microbial agents are molecular in the form of a true solution in a suitable organic solvent. It can also mean that the particles are colloidal in size and distributed throughout a liquid phase in the form of particles held in suspension by wetting agents.

The invention will be better understood with reference to the following examples. It is understood that the examples are intended only to illustrate the invention and it is not intended that the invention be limited thereby.

EXAMPLE 1

To 800 ml (8.8 moles) of a 40% aqueous methylamine solution was added 1000 g (8.4 moles) of 2-nitro-2-methyl-1-propanol. This mixture was heated with stirring for six hours at 55°–60° C. The reaction mixture was cooled and 150 g $Na_2SO_4$ was added and the stirring was continued for thirty minutes. At this time 600 ml benzene was added, filtered, separated and the benzene layer dried over $Na_2SO_4$. The benzene was removed under vacuo and the remaining liquid distilled off at 60° C./10 mm Hg. The product crystallized from the pot residue and was recrystallized from benzene-petroleum ether (3:1). The product was recrystallized three times to yield 217 g of white crystals, melting point 80°–81° C. There was obtained N,2-dimethyl-2-nitro-1-propylamine. The proton magnetic resonance (pmr) spectrum, infra-red absorption spectrum, and mass spectrum were consistent with the proposed structure. The molecular weight by non-aqueous titration was 131.9.

To the compound prepared above, 85.5 g (0.64 mole), was added 200 ml of water and 100 g crushed ice. The pH was lowered to 2 by adding concentrated hydrochloric acid. Another 200 g crushed ice was added and then a solution of 47.2 g sodium nitrite in 100 ml water was added over a five minute period. This mixture was stirred for one hour. Upon cooling in an ice bath, crystals began to form. These were filtered and washed several times with cold water to give 90.7 g of crude product. This was recrystallized from isopropyl alcohol-water (3:1) to give white crystals m.p. 42.5°–43.5° C. There was obtained N-nitroso-N,2-dimethyl-2-nitro-1-propylamine. The pmr and infrared spectra were compatible with the proposed structure.

A solution of the nitroso compound was prepared by dissolving 150 g (0.93 mole) in 500 ml dry methanol. The nitroso compound was reduced at 50° C. and 1500 psi of hydrogen in the presence of 2.7 g Pd on char. The catalyst was removed by filtering the solution and the methanol removed in vacuo to leave 51.9 g of a light green oil which crystallized upon cooling. The product was recrystallized from benzene-petroleum ether (3:1) to give white crystals melting 80.5°–1.5° C. There was obtained what was believed to be 2,3-dihydroxy-1,4,4-trimethyl-1,2,3-triazolidine. The pmr was consistent with the proposed structure. Values for the elements as determined by analysis are given below, along with calculated values for the proposed structure:

|  | C | H | N | O |
|---|---|---|---|---|
| Found, %: | 40.61 | 9.20 | 28.42 | 21.33 |
| Calculated, %: | 40.79 | 8.91 | 28.56 | 21.75 |

The compound prepared above was tested for antibacterial activity by determining the minimum inhibitory endpoint against a variety of representative organisms as set forth below. In the table, the lower figure is the highest concentration tested at which growth occurs and the higher figure is the lowest concentration tested at which no growth occurs.

| Organism | Minimum Inhibitory Concentration, ug/ml |
|---|---|
| *Staphylococcus aureus* | 10–50 |

-continued

| Organism | Minimum Inhibitory Concentration, ug/ml |
|---|---|
| *Streptococcus fecalis* | 100-500 |
| *Streptococcus hemolyticus* | 100-500 |
| *Escherichia coli* | 1-10 |
| *Pasteurella pseudotuberculosis* | 1-10 |
| *Pseudomonas aeruginosa* | 1-10 |
| *Shigella dysenteriae* | 100-500 |
| *Mycobacterium ranae* | 1-10 |

The compound is employed in a cutting oil at a concentration of 1000 ppm to control the growth of bacteria.

EXAMPLE 2

The experiment of Example 1 is repeated in all essential details except that ethylamine is substituted for methylamine. The nitroamine obtained is N-ethyl-2-methyl-2-nitro-1-propylamine. The compound by nitrosation and reduction is active against bacteria and is useful in cutting oils at a concentration of 1000 ppm to control the growth of bacteria.

EXAMPLE 3

The experiment of Example 1 is repeated in all essential details except that 2-nitro-1-ethanol is substituted for 2-nitro-2-methyl-1-propanol on an equimolar basis and n-propylamine is substituted for methylamine on an equimolar basis. There is obtained N-propyl-1-nitroethylamine. The compound obtained upon nitrosation and reduction is active against bacteria and is useful in cutting oils at a concentration of 1000 ppm to control the growth of bacteria.

EXAMPLE 4

The experiment of Example 1 is repeated in all essential details except that 2-nitro-1-butanol is substituted for 2-nitro-2-methyl-1-propanol on an equimolar basis and isopropylamine is substituted for methylamine on an equimolar basis. There is obtained N-isopropyl-2-nitrobutylamine. The compound obtained upon nitrosation and reduction is active against bacteria and is useful in cutting oils at a concentration of 1000 ppm to control the growth of bacteria.

EXAMPLE 5

The experiment of Example 1 is repeated in all essential details except that tris(hydroxymethyl)nitromethane is substituted for 2-nitro-2-methyl-1-propanol on an equimolar basis. There is obtained N-methyl-2-hydroxymethyl-2-nitro-1,3-propanolamine. The compound obtained upon nitrosation and reduction is active against bacteria and is useful in cutting oils at a concentration of 1000 ppm to control the growth of bacteria.

EXAMPLE 6

The experiment of Example 1 is repeated in all essential details except that 2-nitro-2-ethyl-1,3-propanediol is substituted for 2-nitro-2-methyl-1-propanol on an equimolar basis. There is obtained N-methyl-2-ethyl-2-nitro-1,3-propanolamine. The compound obtained upon nitrosation and reduction is active against bacteria and is useful in cutting oils at a concentration of 1000 ppm to control the growth of bacteria.

EXAMPLE 7

The experiment of Example 1 is repeated in all essential details except that n-butylamine is substituted for methylamine on an equimolar basis. There was obtained a compound believed to be N-butyl-N-nitroso-2-hydroxylamino-2-methyl-propylamine. It was active against both bacteria and fungi as shown by the following anti-microbial spectrum.

| Organism | Minimum Inhibitory Concentration, ppm |
|---|---|
| *Staphylococcus aureus* | 100-500 |
| *Streptococcus fecalis* | 100-500 |
| *Streptococcus hemolyticus* | 100-500 |
| *Escherichia coli* | 500-1000 |
| *Pasteurella pseudotuberculosis* | 100-500 |
| *Pseudomonas aeruginosa* | 100-500 |
| *Shigella dysenteriae* | 100-500 |
| *Mycobacterium ranae* | 10-50 |
| *Aspergillus niger* | 500-1000 |
| *Candida albicans* | 500-1000 |
| *Penicillium species* | 100-500 |
| *Fusarium oxysporum* | 100-500 |

EXAMPLE 8

The experiment of Example 1 is repeated in all essential details except that aniline is substituted for methylamine on an equimolar basis. The compound thereby obtained is active against bacteria and fungi and is useful to control the growth of these organisms.

EXAMPLE 9

The experiment of Example 1 is repeated in all essential details except that toluidine is substituted for methylamine on an equimolar basis. The compound thereby obtained is active against bacteria and fungi and is useful to control the growth of these organisms.

EXAMPLE 10

The experiment of Example 1 is repeated in all essential details except that xylidine is substituted for methylamine on an equimolar basis. The compound thereby obtained is active against bacteria and fungi and is useful to control the growth of these organisms.

EXAMPLE 11

The experiment of Example 1 is repeated in all essential details except that benzylamine is substituted for methylamine on an equimolar basis. The compound thereby obtained is active against bacteria and fungi and is useful to control the growth of these organisms.

I claim:

1. A method of controlling the growth of bacteria by applying to them or to the environment inhabited by them a growth-inhibiting amount of the product prepared by the process consisting of the steps of (a) reacting a nitroalcohol of the formula

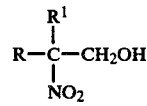

where R and $R^1$ can be hydrogen, methyl, ethyl or hydroxymethyl in about a 1:1 mole ratio with an amine represented by the formula $R^2NH_2$ where $R^2$ is alkyl of from 1 to 4 or more carbon atoms, phenyl, benzyl, toluyl, or xylyl at about 50°-70° thereby effecting formation of a nitroamine, (b) reacting the nitroamine with nitrous acid at about 0°–5°, thereby forming a nitroso compound, and (c) reducing the nitroso compound.

2. The method of claim 1 wherein $R^2$ is methyl.
3. The method of claim 1 wherein $R^2$ is ethyl.
4. The method of claim 1 wherein $R^2$ is propyl.
5. The method of claim 1 wherein $R^2$ is butyl.
6. The method of claim 1 wherein R is hydrogen.
7. The method of claim 1 wherein R is methyl.
8. The method of claim 1 wherein R is ethyl.
9. The method of claim 1 wherein R is hydroxymethyl.
10. The method of claim 1 wherein $R^1$ is hydrogen.
11. The method of claim 1 wherein $R^1$ is methyl.
12. The method of claim 1 wherein $R^1$ is ethyl.
13. The method of claim 1 wherein $R^1$ is hydroxymethyl.
14. The method of claim 1 wherein $R^2$ is phenyl.
15. The method of claim 1 wherein $R^2$ is toluyl.
16. The method of claim 1 wherein $R^2$ is xylyl.
17. The method of claim 1 wherein $R^2$ is benzyl.

* * * * *